US00PP32635P3

(12) United States Plant Patent
Stemkens

(10) Patent No.: US PP32,635 P3
(45) Date of Patent: Dec. 15, 2020

(54) ***VERBENA* PLANT NAMED 'VEAZ0057'**

(50) Latin Name: *Verbena hybrida*
Varietal Denomination: VEAZ0057

(71) Applicant: SYNGENTA CROP PROTECTION AG, Basel (CH)

(72) Inventor: Henricus Godefridus Wilhelmus Stemkens, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,751

(22) Filed: Jun. 3, 2019

(65) Prior Publication Data

US 2020/0170164 P1 May 28, 2020

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86; A01H 5/02
See application file for complete search history.

*Primary Examiner* — Keith O. Robinson
(74) *Attorney, Agent, or Firm* — Dale Skalla

(57) ABSTRACT

A new *Verbena* plant named 'VEAZ0057' particularly distinguished by large sized flowers, of which the upper 2 petals are red colored and the lower 3 are pink colored, dark green, undivided leaves and a semi-trailing and vigorous plant habit.

1 Drawing Sheet

Latin name of the genus and species of the plant claimed: *Verbena hybrida.*

Varietal denomination: 'VEAZ0057'.

BACKGROUND OF THE NEW PLANT

The present invention comprises a new *Verbena*, botanically known as *Verbena hybrida*, and hereinafter referred to by the variety name 'VEAZ0057'.

'VEAZ0057' is a product of a planned breeding program. The new cultivar has large sized flowers, of which the upper 2 petals are red colored and the lower 3 are pink colored, dark green, undivided leaves and a semi-trailing and vigorous plant habit.

'VEAZ0057' originated from a cross made in August 2014 in a greenhouse in Enkhuizen, The Netherlands. The female parent was an unpatented propriety plant named 'T0975-3' having a scarlet color and a compact plant habit. The male parent was a cloud of pollen of all material in the insect-pollination-isolation.

Seeds of the cross were sown in March 2015 and one plant was selected in May 2015 which became 'VEAZ0057'.

The first act of asexual reproduction of 'VEAZ0057' was accomplished when vegetative cuttings were propagated in July 2015 in a greenhouse in Enkhuizen, The Netherlands.

BRIEF SUMMARY OF INVENTION

Horticultural examination of plants grown from cuttings of the plant initiated in the fall of 2015, and continuing thereafter, has demonstrated that the combination of characteristics as herein disclosed for 'VEAZ0057' are firmly fixed and are retained through successive generations of asexual reproduction.

'VEAZ0057' has not been observed under all possible environmental conditions. The phenotype may vary significantly with variations in environment such as temperature, light intensity, and day length.

A Plant Breeder's Right for this cultivar was applied for in the European Union on Nov. 23, 2018, No. 2018/3070. 'VEAZ0057' has not been made publicly available prior to the effective filing date of this application, notwithstanding any disclosure that may have been made less than one year prior to the effective filing date of this application by the inventor or another who obtained 'VEAZ0057' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0057' with colors being as true as possible with an illustration of this type.

Figure 1:
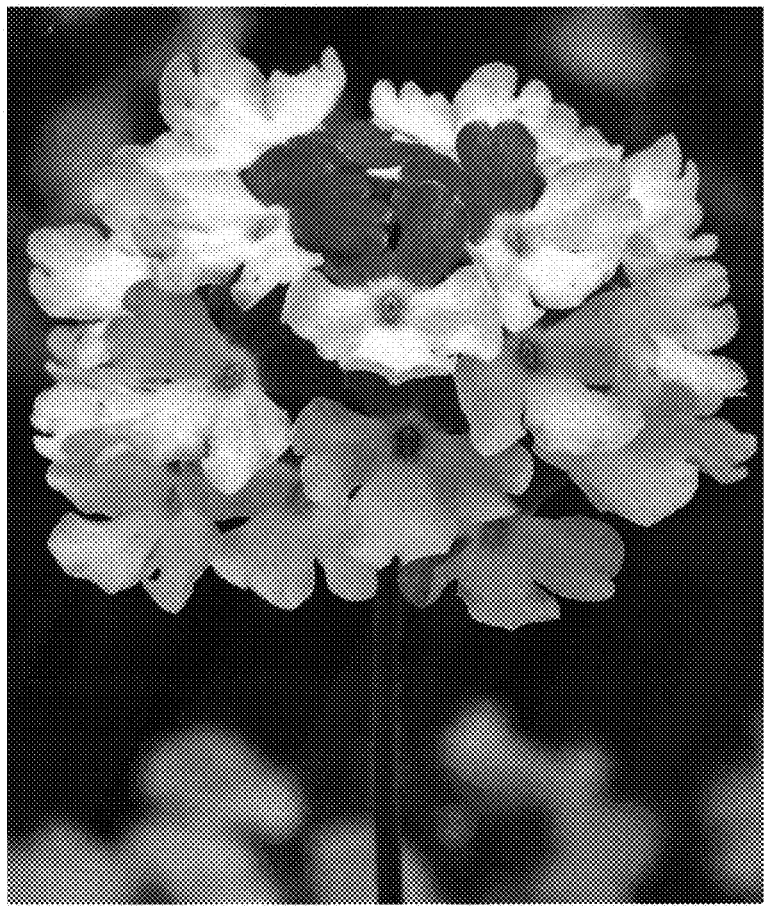
Figure 2:
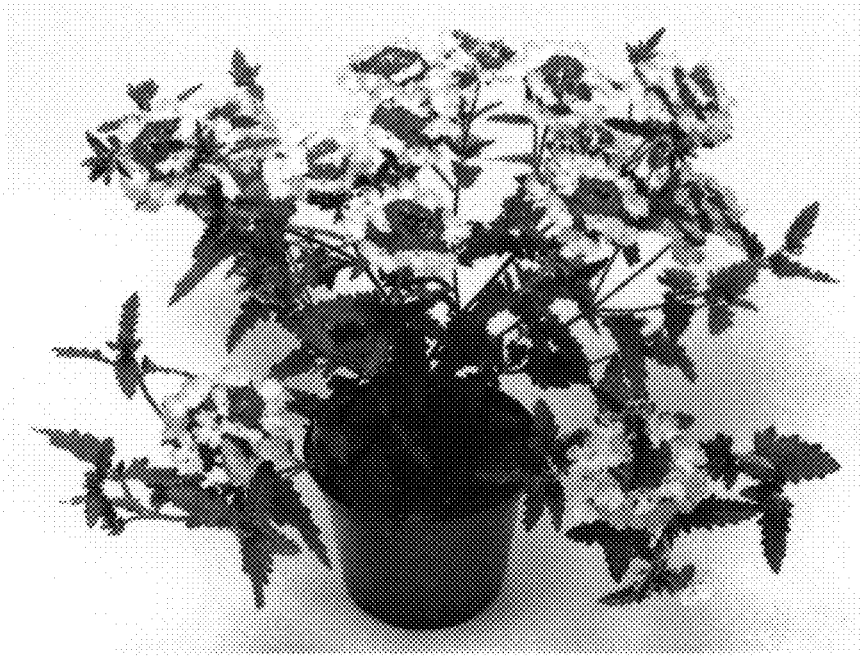

The photographic drawing in FIG. 1 shows a close view of an inflorescence of the new plant, and in FIG. 2 a whole flowering plant.

The aforementioned photographs were taken in May 2018 in Andijk, The Netherlands. The plants were about 12 weeks old and were grown in 12 cm pots.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0057' AND A MOST SIMILAR VARIETY

| | 'VEAZ0057' | 'VEAZ0009', U.S. Plant Pat. No. 23,575 |
|---|---|---|
| Branching: | More branches per plant | Less branches per plant |
| Flower, size: | Larger | Smaller |
| Plant, size: | Larger | Smaller |
| Flowering: | Less flushes | More flushes |

Plant:

*Form, growth and habit.*—Herbaceous, semi-trailing and vigorous.

*Plant height.*—25.0 cm.

*Plant height (inflorescence included).*—29.0 cm.

*Plant width.*—59.0 cm.

Roots:

*Number of days to initiate and produce roots.*—11-13 days at about 21 degrees C.

*Type.*—Fine, fibrous, free branching.

*Color.*—RHS N155B.

Foliage:

*Arrangement.*—Opposite, simple.

*Immature, leaf color, upper surface.*—RHS 143C.

*Immature, leaf color, lower surface.*—RHS 137B.

*Mature, leaf color, upper surface.*—RHS 143B.

*Mature, leaf color, lower surface.*—RHS 137C.

*Length.*—Approximately 4.2 cm.

*Width.*—2.2-3.5 cm.

*Shape.*—Hastate.

*Base shape.*—Obtuse.

*Apex shape.*—Obtuse.

*Margin.*—Lobed.

*Texture, upper surface.*—Pubescent.

*Lower surface.*—Pubescent.

*Color of veins, upper surface.*—RHS 144B.

*Color of veins, lower surface.*—RHS 144A.

*Pattern of veining.*—Pinnate.

*Petiole color.*—RHS 144B.

*Petiole length.*—0.7 cm.

*Petiole width.*—0.45 cm.

*Texture.*—Hirsute.

Stem:

*Branching characteristics.*—Side branches develop potentially at each node.

*Quantity of main branches per plant.*—18-22.

*Anthocyanin of the stem.*—Absent.

*Color of stem.*—RHS 144C.

*Stem length.*—28.0-35.0 cm.

*Stem width.*—0.3 cm.

*Length of internodes.*—1.4-2.2 cm.

*Texture.*—Hirsute.

*Color of peduncle.*—RHS 138C.

*Length of peduncle.*—2.4-3.2 cm.

*Peduncle diameter.*—0.2 cm.

*Texture.*—Glandular hairs.

Inflorescence:

*Type.*—Umbel-like, but actually a spike, umbrella-shaped.

*Blooming habit.*—Flowers develop continuously during the summer months.

*Lastingness of individual blooms on the plant.*—About 3-4 days in the greenhouse.

*Fragrance.*—None.

*Number of inflorescences per plant.*—34-45 at various stages at development.

*Horizontal diameter of inflorescence.*—4.2-4.7 cm.

*Depth of inflorescence.*—3.9 cm.

*Number of florets and buds per inflorescence.*—Approximately 26-33.

Bud:

*Color.*—RHS N155A.

*Length.*—0.2 cm.

*Width.*—0.3 cm.

*Shape.*—Tubular with bulbous apex.

Floret:

*Form.*—Sessile; salver-shaped, composed of 5 partly fused petals with a base of a narrow tube.

*Immature color, upper surface.*—Upper 2 petals RHS 46A. Lower 3 petals from RHS 51C to RHS 54B.

*Immature color, lower surface.*—RHS N155A.

*Mature color, upper surface.*—Upper 2 petals RHS 46A. Lower 3 petals from RHS 51C to RHS 54A.

*Mature color, lower surface.*—RHS N155B.

*Floret diameter.*—5.9 cm.

*Floret length (depth).*—3.7 cm.

*Petal length.*—0.8 cm.

*Petal width.*—0.4 cm.

*Shape.*—Obcordate.

*Apex shape.*—Emarginate.

*Margin.*—Entire.

*Petal texture, upper surface.*—Smooth.

*Petal texture, lower surface.*—Smooth.

*Longitudinal axis of the corolla lobe.*—Incurved.

*Corolla tube length.*—2.4 cm.

*Corolla tube width.*—0.3 cm.

*Corolla tube color inside.*—RHS 47B.

*Tube color outside.*—RHS 47B.

*Corolla texture, inside.*—Pubescent.

*Corolla texture, outside.*—Pubescent.

*Eye of the corolla.*—Present.

*Diameter.*—55 mm.

*Color.*—White, RHS 155 in some flowers the eye is interrupted with a light red-purple (RHS N57B) spot or stripe.

*Throat hair color.*—RHS 155C but whiter.

Calyx:

*Type.*—Five sepals whose margins are fused to each other along their length, with a transparent membrane of less than 0.15 cm in width and with one smaller sepal attached to the base of the calyx.

*Color of sepals.*—RHS 137C.

*Length of sepals.*—1.1 cm.

*Width of sepals.*—0.2 cm.

*Sepal shape.*—Fused, linear.

*Apex shape.*—Acute.

*Margins.*—Entire.

*Texture.*—Densely covered with very short glandular hair.

Reproductive organs:

*Gynoecium.*—

*Pistil.*—1.

*Pistil length.*—1.5 cm.

*Style color.*—RHS 144C.

*Style length.*—1.6 cm.

*Stigma color.*—RHS 143B.

*Ovary color*.—RHS 144B.
*Ovary length*.—0.15 cm.
*Ovary width*.—0.1 cm.
*Androecium*.—
*Stamens*.—Anthers and filaments fused to upper half of corolla tube; four anthers with two pollen sacs per anther.
*Color of filaments*.—RHS 151C.
*Filament length*.—0.2 cm.
*Anther color*.—RHS 151C.
*Anther length*.—0.1 cm.
*Pollen amount*.—None observed.
Fertility/seed set: Neither seed nor fruit production has been observed.
Disease/pest resistance: Resistance to pathogens and pests common to *Verbena* has not been observed.

What is claimed is:

1. A new and distinct variety of *Verbena* plant named 'VEAZ0057' substantially as illustrated and described herein.

* * * * *